United States Patent
Young et al.

[19]

[11] Patent Number: 5,591,635
[45] Date of Patent: Jan. 7, 1997

[54] METHODS AND APPARATUSES FOR RAPID COMPOSTING WITH CLOSED AIR LOOP CIRCULATION FOR POSITIVE CONTROL

[75] Inventors: Richard N. Young, Atlanta, Ga.; Thomas J. Irwin, II, Newton, Pa.

[73] Assignee: DBS Manufacturing, Inc., Forest Park, Ga.

[21] Appl. No.: 323,451

[22] Filed: Oct. 14, 1994

[51] Int. Cl.⁶ .................................................. G01N 33/00
[52] U.S. Cl. .................................. 435/286.1; 435/286.6; 435/286.7; 435/290.2; 435/290.3
[58] Field of Search .................................... 435/312, 316, 435/286.1, 286.6, 286.7, 290.2, 290.3

[56] References Cited

U.S. PATENT DOCUMENTS

| | | | |
|---|---|---|---|
| 2,929,688 | 3/1960 | Riker et al. | |
| 2,948,593 | 8/1960 | Larson | 435/290.3 |
| 3,245,759 | 4/1966 | Eweson | 435/290.3 |
| 3,272,740 | 9/1966 | Gitchel et al. | 210/3 |
| 3,533,775 | 10/1970 | Brown | 71/13 |
| 4,072,494 | 2/1978 | Gujer | 71/9 |
| 4,255,389 | 3/1981 | Jung et al. | 422/209 |
| 4,493,770 | 1/1985 | Moilliet | 210/603 |
| 4,668,388 | 5/1987 | Dibble et al. | 210/150 |
| 4,780,415 | 10/1988 | Ducellier et al. | 435/166 |
| 5,145,581 | 9/1992 | Novy et al. | 210/609 |
| 5,169,782 | 12/1992 | Murphy et al. | 435/312 |
| 5,292,637 | 3/1994 | Bohnensieker | 435/3 |
| 5,427,947 | 6/1995 | Dalos | 435/312 |
| 5,459,071 | 10/1995 | Finn | 435/290.2 |

*Primary Examiner*—David A. Redding
*Attorney, Agent, or Firm*—Needle & Rosenberg, P.C.

[57] ABSTRACT

A reaction vessel for biologically decomposing a material comprises a frame, an airtight housing rotatably mounted on the frame defining an enclosure therein, and a device for controlling environmental conditions within the enclosure so that biological decomposition of the material can occur at a controlled rate. Air is circulated through the enclosure in a closed loop so that air leaving the enclosure will be recirculated back into the enclosure. A computer controls the oxygen level of the air inside the enclosure, the humidity of the air inside the enclosure, the temperature of the air inside the enclosure, and the carbon dioxide level of the air inside the enclosure. The housing is disposed at an incline relative to the frame so that the material introduced into the enclosure proximal to the higher portion of the housing tends to flow toward the lower portion of the housing. A separating wall is disposed within the enclosure, forming therein a first chamber and a second chamber. A screw conveyor is provided for moving the material from the first chamber to the second chamber. The conveyor is secured to the housing so that as the material is moved from the first chamber to the second chamber the housing remains airtight.

27 Claims, 3 Drawing Sheets

5,591,635

METHODS AND APPARATUSES FOR RAPID COMPOSTING WITH CLOSED AIR LOOP CIRCULATION FOR POSITIVE CONTROL

BACKGROUND OF THE INVENTION

1. Field of the Invention

This invention relates to a method and apparatus for composting. More particularly, this invention relates to continuous and cost-effective composting of large quantities of waste material while maintaining maximum control over the reaction parameters by using closed loop air circulation.

2. The Prior Art

General methods and apparatuses for composting have existed many years. Composting may even be accomplished without any particular apparatus at all. For instance, windrows can be used. Windrows is the composting of a material by laying it out on a field and periodically turning it over with a tractor However, windrows suffer from a number of deficiencies. First, windrows are highly susceptible to adverse weather conditions. Furthermore, the biological and chemical makeup of the material to be composted cannot be assayed and used to adjust the composting parameters. Mixing of the windrowed material may only be accomplished by manually overturning the windrows. Manual overturning often leaves partially composted material in a non-homogenous state. This non-homogeneity leads to non-uniform temperature distribution as well as anaerobic pockets in the material. These pockets create the obnoxious odors associated with open-air composting methods. Therefore, a need exists for an improved composting method which overcomes the deficiencies of windrowing.

Converting sewage sludge into usable humus fertilizer is an environmentally sound goal. This conversion is accomplished via aerobic stabilization and rotting, i.e., composting. In actual use, static methods of composting (such as windrowing) remain unsatifactory on both the technical and economic level. The dissatisfaction has lead to efforts to develop machine composting.

Since the 1970s, composting has become an important method for stabilizing and processing municipal sewage. See EPA, *Summary Report on In-Vessel Composting of Municipal Wastewater Sludge,* Risk Reduction Engineering Laboratory, Center for Environmental Research Information, September 1989. The technology has developed extremely rapidly, from less than 10 facilities in 1975 to nearly 200 under design or in operation in 1989. Because of odor, labor, and materials-handling problems, designers are producing composting systems built to contain the materials within a vessel. These systems extensively use conveyors and other materials-handling equipment. Although evolution of "in-vessel" systems is very rapid, municipalities continue to face serious problems in dealing with odors, removing moisture, handling the materials in the system and marketing the product.

In-vessel composting is an integrally related system which includes:

Materials (sludge cake, amendment, and recycle)

Materials handling (including storage, mixing and conveyance)

Reactor system

Aeration system

Odor control system

Exterior curing/storage facilities

Marketing

A general composting process begins with the mixing of sludge cake, amendment, if any, (e.g., sawdust) and recycling it in an aerated reactor. Air is diffused into the reactor for temperature control, moisture removal and biological metabolism. Air from within the reactor is then exhausted to an odor treatment system before being dispersed into the atmosphere. After a desired detention time within the vessel, the material is removed from the reactor for further curing/storage.

Composting occurs in multiple stages. The first stage is a high-rate phase. This phase is characterized by high oxygen uptake rates, high temperatures, rapid degradation of biodegradable volatile solids and high odor production. The second stage is a curing phase. This phase is characterized by lower temperatures, reduced oxygen uptake rates and a lower, but significant, potential for odor production.

In machine composting methods, the user can control mixing, ventilation, oxygen supply, moisture content and temperature to more reliably, rapidly and economically transit the two phases and, therefore, perform composting. As noted above with respect to windrows, the major problem with composting is the formation of anaerobic zones as a result of insufficient mixing. Despite numerous efforts, none of the existing machine solutions provides a truly simple, economical, elegant solution to the general problems associated with composting.

Other in-vessel composting apparatuses solve, at least to some degree, some of the problems of windrowing. For instance, the device of U.S. Pat. No. 3,533,775 (the '775 patent) to Brown provides a process for aerobically preparing fertilizer from a mixture of waste containing paper and sewage sludge. Salvageable materials in the municipal waste are "manually, pneumatically, mechanically, or electromagnetically removed." The remainder is comminuted and any paper and film plastic is removed and burned. The heat from burning is used to evaporate water from the sewage sludge or for drying the compost. The remaining waste is then deposited in a series of ½" thick layers in a composting tank. Sewage sludge is added. Oxygen-enriched air is introduced through a false bottom to accelerate aeration. An agitator is used to mix the compost and accelerate decomposition. The compost is finally dried with hot air, ground, and bagged as fertilizer.

However, the device disclosed in the '775 patent does not use a rotating vessel. The lack of rotation of the entire vessel necessitates the use of an external agitator. The likelihood of anaerobic pockets is substantial. Furthermore, it is unlikely that homogenous aeration will occur considering the density of partially composted materials.

U.S. Pat. No. 3,272,740 (the '740 patent) to Gitchel et al. discloses a process for treatment of sewage sludge. First, sewage sludge solids are cured by either settling on a sand bed or by rotary drum filtration and then are dried to obtain a completely dry product. Wet air oxidation reduces the biochemical and chemical oxygen demand of the sewage sludge. Wet air oxidation involves oxidation at 100°–150° C. with gaseous oxygen in the presence of water. In wet air oxidation, some of the water is kept in a liquid state by performing the oxidation under pressure. The '740 device achieves a continuous partial wet air oxidation. To produce a "desirable, innocuous organic sludge," the oxygen supplied during wet air oxidation is limited to about 5 to 45 percent of the chemical oxygen demand of the sludge. A continuous flow of a source of known chemical oxygen demand is varied for purposes of equilibrating the oxygen consumption in the reaction chamber. The '740 patent also discloses the variation of gaseous oxygen flow rate while maintaining a constant sludge flow rate. Heat exchange is used for temperature regulation.

Unlike the device disclosed in the '775 patent, the device disclosed in the '740 patent is capable or air-tight and even pressurized operation. In addition, limitation of oxygen supply is discussed and the device is capable of continuous operation. However, no means for removing liquids or gases from the vessel is disclosed. Most significantly, wet air oxidation is an entirely different process from composting. Wet air oxidation is a chemical process. Composting is a biological process. The temperature ranges needed for wet air oxidation are unsuitable for composting. Therefore, there remains a need for a biological composting apparatus which is capable of continuous pressurized operation and into and from which reactants such as air and water can be added or removed as appropriate.

U.S. Pat. No. 2,929,688 (the '688 patent) to Riker et at. discloses an aerobic composing apparatus. Sewage sludge is first passed through a liming tank and is then dewatered before being passed to a mixer. The mixer combines garbage and sewage sludge and, in addition, heats the mixture. The raw organic material to be composted is then conveyed to the composting tanks and gravity dropped into the upper compartments of the tanks. The tanks are made up of a series of vertically spaced compartments. Each compartment has an exhaust vent to assist in circulation and the exhaust of air and gases. A liquid delivery line is also attached to each compartment for bringing water or other compounds into the compartment. Air lines are positioned across each compartment and compressed air is fed into the compartment through these lines. Each compartment contains a mechanical agitator. Finally, a screw type conveyor is used to move organic material.

The '688 device consists of vertically disposed vessels and, thus, agitation occurs only via mechanical means within the vessel. The device is not air-tight. The energy costs of manual agitation make systems like the '688 system inefficient.

U.S. Pat. No. 4,072,494 (the '494 patent) to Gujer discloses another device for composting of high water content sludge. The device involves mixing the sludge with oxygen-containing gas under pressure in a gas impermeable device. Excess heat is removed in the device disclosed in the '494 patent by simply cooling the device's walls. Cooling or heating air is also disclosed as a way to accomplish heat exchange. The device itself is shaped as a gas-tight drum having a horizontal axis of rotation. The rotation is accomplished using rollers and the drum rotates at about 10 to 15 RPM. Scoop-like protuberances are present on the interior walls of the drum and are used to scoop up the substantially liquid sludge and thereby aerate it.

The device disclosed in the '494 patent, however, would be unsuitable for composting low water content biomass. The device disclosed in the '494 patent lacks means for controlling liquid flow and also lacks means for moving partially composted material within the composter. No staging process is contemplated. This is understandable because the high water content sludge contemplated for use in the device disclosed in the '494 patent presents a substantially higher viscosity than normal composting materials. Therefore, gravity flow would be sufficient to move the material along the drum. In addition, maintaining the high rotational speed of the composter is likely quite expensive in terms of energy needed, thereby decreasing the efficiency of the system. Furthermore, the use of scoops is only useful for high water content sludge. For substantially solid biomass, these scoops would either fail to perform their intended function or would mechanically fail from the enormous stresses placed upon them by moving the biomass. The device disclosed in the '494 patent is a wet composting device, operable on materials having from 5 to 8% (but no more than 25%) solids content. Biological degradation, however, requires a maximum of 22% water content for viability of active bacteria.

Therefore, it is highly desirable to provide a composter capable of continuous operation upon a substantially solid biomass having a high solids content and, therefore, low viscosity. It is desirable that such a device allow for control over liquid content within the vessel, as well as having the positive capability to move material from one part of the vessel to another. It is also desirable to have a device which is capable of operating with a minimum of energy overhead.

SUMMARY OF THE INVENTION

The above-noted disadvantages of the prior art are overcome by the present invention, a reaction vessel for biologically decomposing a material. The reaction vessel has a frame, a substantially airtight housing rotatably mounted on the frame defining an enclosure therein, and means for controlling environmental conditions within the enclosure so that biological decompostition of the material can occur at a controlled rate. The housing has a first aperture for receiving the material into the enclosure and a second aperture for discharging the material from the enclosure.

A means for agitating the material in the enclosure by rotating the housing is provided. The means for rotating the housing, which could comprise a motor, has a means to control the rotational speed of the housing. The motor is coupled to the housing so that the motor causes the housing to rotate at a rate determined by a current input to the motor. The current is representative of the desired speed of the motor and is generated by a relay that is responsive to a computer-generated speed control signal. Rotational speed control can also be accomplished by other means, including selective motor on/off cycling and hydraulic control, depending on the application and the type of motor used.

The environmental conditions within the enclosure are controlled by a means for circulating air through the enclosure in a closed loop so that air leaving the enclosure will be recirculated back into the enclosure and a means to control the air recirculation rate within the enclosure. The air recirculation rate is controlled by a means which comprises a computer which generates a blower speed control signal representative of a predetermined blower speed and a blower, in fluid communication with the air circulating means. The blower is responsive to the blower speed control signal and causes air to flow through the air circulating means at a rate corresponding to the blower speed control signal.

The means for controlling the environmental conditions within the enclosure also comprises means for controlling the oxygen level of the air inside the enclosure. The oxygen level control means senses the oxygen level with an oxygen sensor that generates a signal representative of the oxygen level inside the enclosure. A computer, responsive to the signal from the oxygen sensor compares the received signal from the oxygen sensor to a preselected value of oxygen level and then generates an oxygen activation signal that activates an oxygen adding means when the oxygen level falls below the preselected value of oxygen level. The oxygen adding means comprises an oxygen supply and an electrically activated valve responsive to the oxygen activation signal. The oxygen adding means is in fluid communication with the oxygen supply and the enclosure, and it allows oxygen from the oxygen supply to pass into the enclosure upon receiving the oxygen activation signal.

The means for controlling the environmental conditions also comprises means for controlling the humidity of the air inside the enclosure. The humidity control means comprises a humidity sensor that generates a signal representative of the humidity of the air inside the enclosure, a means for adding water to the air in the enclosure, a means for removing humidity from the air in the enclosure, and a computer. The computer is responsive to the signal from the humidity sensor and compares the received signal from the humidity sensor to a preselected value of humidity and then generates either a humidity addition activation signal that activates the water adding means when the humidity falls below a first preselected value of humidity level or a humidity removal activation signal that activates the means for removing humidity when the humidity rises above a second preselected humidity level. The water adding means comprises a water supply, a water spray nozzle in fluid communication with the enclosure, and an electrically activated valve responsive to the water spray activation signal, in fluid communication with the water supply and the water spray nozzle, that allows water from the water supply to pass through the water spray nozzle into the enclosure upon receiving the water spray activation signal. The humidity removing means comprises a dehumidifier through which the air recirculating in the enclosure passes.

The means for controlling the environmental conditions also comprises means for controlling the temperature of the air inside the enclosure. The temperature control means has a temperature sensor that generates a signal representative of the temperature of the air inside the enclosure, a means for adding heat to the air in the enclosure, a means for removing heat from the air in the enclosure, and a computer, responsive to the signal from the temperature sensor. The computer compares the received signal from the temperature sensor to a first preselected value of temperature and a second preselected value of temperature, and then generates either a heat addition activation signal that activates the heat adding means when the temperature falls below the first preselected value of temperature or a heat removal activation signal that activates the means for removing heat when the temperature rises above the second preselected value temperature. The heat adding means comprises a heater in thermal communication with the enclosure and responsive to the heat addition activation signal and adds heat to the enclosure upon receiving the heat addition activation signal. The heat removing means comprises a heat exchanger in thermal communication with the enclosure responsive to the heat removing activation signal which removes heat from the enclosure upon receiving the heat removing activation signal.

The means for controlling the environmental conditions also comprises means for controlling the carbon dioxide level of the air inside the enclosure. The carbon dioxide level control means comprises a carbon dioxide level sensor that generates a signal representative of the carbon dioxide level of the air inside the enclosure, a means for removing carbon dioxide from the air in the enclosure, and a computer, responsive to the signal from the carbon dioxide level sensor. The computer compares the received signal from the carbon dioxide level sensor to a preselected value of carbon dioxide level and then generates a carbon dioxide removal activation signal that activates the carbon dioxide removal means when the carbon dioxide level rises above the preselected value. The means for removing carbon dioxide could be a vent connected to a valve which is responsive to the carbon dioxide removal activation signal that allows air from inside the enclosure to exit the enclosure and a fresh air intake used to allow replacement air to enter the enclosure when the carbon dioxide level of the air in the enclosure rises above the preselected value of carbon dioxide level. A $CO_2$ scrubber could also be used, depending on the application.

The axis of rotation of the housing may be disposed at an incline relative to the frame so that the material introduced into the enclosure proximal to the higher portion of the housing tends to flow toward the lower portion of the housing. A hydraulic jack, or other means, such as a mechanical lift, may be provided to adjust the mount of inclination of the housing.

One or more separating walls may be disposed within the enclosure, generally perpendicular to the axis of rotation, forming a first chamber and a second chamber, each capable of containing the material. This would be the ideal configuration for a continuous processing method, wherein material to be processed is continuously fed into one end of the enclosure while processed material is continuously removed from the other end of the enclosure. With a multi-chambered configuration, a means for moving the material from the first chamber to the second chamber, secured to the housing so that as the material is moved from the first chamber to the second chamber while the housing remains airtight, may be provided. Such a means could comprise a screw-type conveyor or a flat conveyor disposed within the enclosure.

Some types of material to be processed, such as municipal waste, form clumps during processing. These clumps can interfere with decomposition. Therefore, one or more protuberances may be placed on the inside surface of the enclosure to break up clumps of the material as the enclosure is rotated.

A method of composting, in accordance with the invention, uses the following steps: introducing a material to be composted into an airtight vessel, rotating the vessel, and continuously monitoring the environmental conditions inside the vessel. Depending upon the conditions inside the vessel, one or more of the following steps is performed: introducing reactants, such as nitrogen or enzymes, into the vessel, removing reactants from the vessel, adding heat to the vessel, removing heat from the vessel, adding water to the vessel, removing water from the vessel, adding oxygen to the vessel, and removing carbon dioxide from the vessel. The composter of the present invention may be operated at atmospheric pressure, elevated pressure or at a partial vacuum.

It is an object of the present invention to provide a reaction vessel for biologically decomposing material in which the environmental conditions are controllable in order to control the rate of decomposition.

It is also an object of the present invention to provide an air tight reaction vessel that controls the escape of gaseous products of the decomposition process.

It is also an object of the present invention to provide a method of composting organic material in a controlled fashion.

These and other objects will become apparent from the following description of the preferred embodiment taken in conjunction with the following drawings, although variations and modifications may be effected without departing from the spirit and scope of the novel concepts of the disclosure.

DETAILED DESCRIPTION OF THE INVENTION

Figure 1:
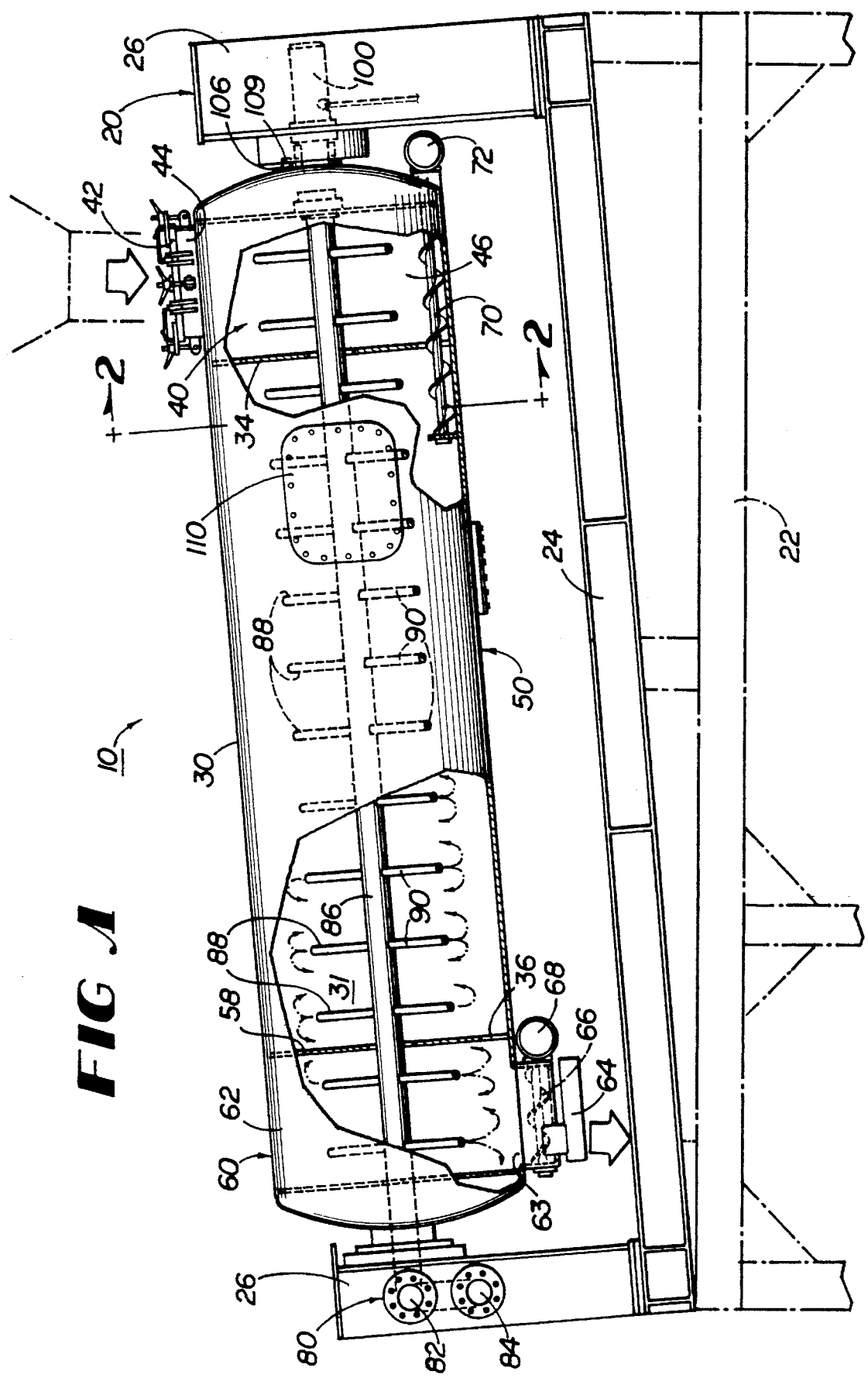
FIG. 1 is a side elevational partial cut-away view of a reaction vessel in accordance with the present invention.

The invention is now described in detail. Referring to the drawings, like numbers indicate like parts throughout the views.

In one preferred embodiment of the present invention 10, as shown in FIG. 1, a substantially cylindrical housing 30, defining therein an enclosure 31, is rotatably mounted on a frame 20. The frame 20 has a substantially horizontal sub-frame 22 that supports an inclined portion 24 and two upright support stantions 26. The housing 30 is vertically and laterally supported by a shaft 33 affixed to each side of the housing 30 and journaled into a beating 32 affixed to each of the upright support stantions 26.

Figure 2:
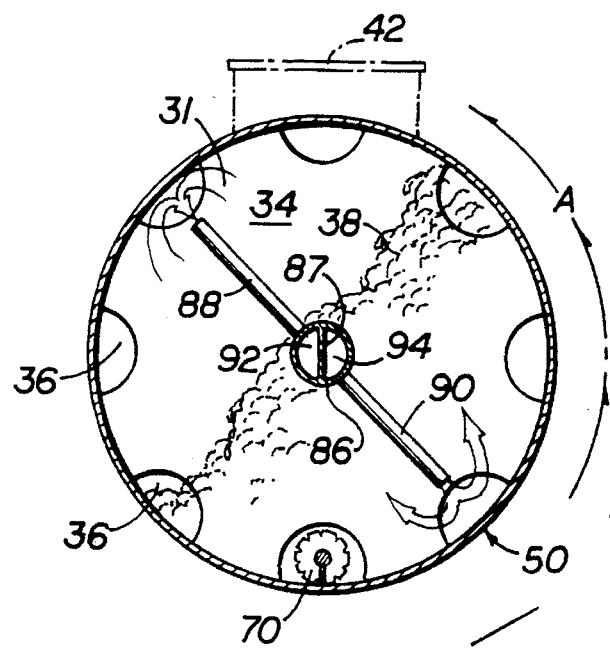
FIG. 2 is a cross sectional view of the present invention taken along lines 2—2.

The housing 30 has a receiving section 40 which comprises a receiving hatch 42 that opens to a receiving aperture 44 through which material may be introduced into the enclosure 31. If the embodiment is configured for continuous processing, a first wall 34 may be disposed within the enclosure 31, substantially perpendicular to the axis of rotation, thereby defining a receiving chamber 46. Referring to FIG. 2, The wall 34 has a plurality of openings 36 passing through it to allow the material being decomposed 38 to pass out of the receiving chamber 46. A material conveyor also may be used to move material out of the receiving chamber 46. Referring again to FIG. 1, such a material conveyor could comprise a screw auger 70 driven by a motor 72. If the embodiment is configured for processing in the batch mode, the first wall 34 is unnecessary, as the enclosure 31 need have only one chamber.

Disposed within the enclosure 31 is a reaction chamber 50 in which the material to be composted undergoes biological decomposition. In one preferred embodiment, the reaction chamber 50 is disposed between the first wall 34 and a second wall 58. In this embodiment, a discharge section 60 comprises a discharge chamber 62 defined by the second wall 58. Properly decomposed material in the discharge chamber 62 passes through a discharge aperture 63 into a discharge conveyor 66, driven by a motor 68, and through a gate 64 into a container used to carry off the composted material (not shown).

If sewage, or other sticky sludge, is to be treated, some form of comunuter (not shown) should be disposed within the enclosure 31, preferably near to the discharge section, to break up any balls that form in the material. This comunuter could comprise a rotating shaft with a plurality of radial blades extending outward from the shaft.

The rate of decomposition of the material inside the enclosure 31 is controlled by controlling the rotation rate of the housing 30 and the environmental conditions within the enclosure 31. The environmental conditions controlled include: the temperature, the humidity, the oxygen ($O_2$) content of the air, and the carbon dioxide ($CO_2$) content of the air. In some applications, the rate of change of the $CO_2$ level indicates the degree of decomposition. These conditions are controlled by monitoring and modifying air in a closed-loop air system 80 that circulates air within the enclosure 31. In alternate embodiments, other gasses, such as ammonia, hydrogen sulfide and methane, are monitored.

Hydrogen sulfide and methane would be likely by-products of an anaerobic decomposition. If the present invention is used in soil remediation, the process may be started anaerobically and, after the completion of anaerobic decomposition, switched to an aerobic process. Therefore, in such an application, the monitoring of hydrogen sulfide and methane levels would be important.

The air system 80 is maintained as a closed-loop system to prevent the escape of any undesirable gasses. Air entering the enclosure 31 passes through an air introduction flange 82 into a bifurcated supply/return manifold 86 which comprises a pipe divided along its axis by a manifold wall 87. As shown in FIG. 2, the air passes through a supply side 94 of the manifold wall 87 into a plurality of supply pipes 90 where the air is discharged into the enclosure 31 via the pile of material being decomposed 38. The air filters through the material 38 and returns to the manifold 86 through a plurality of return pipes 88 into a return side 92. As shown in FIG. 1, the air then exits the enclosure 31 through an air return flange 84.

The housing 30 is continuously rotated by a motor 100 supported by one of the upright stantions 26 and coupled to the housing 30. The motor 100 may be an electric motor or any suitable device for causing the housing 30 to rotate.

An access and inspection hatch 110 is attached to the housing 30, allowing access for inspection and repair of the system. In some embodiments, this could be a window to allow for continuous inspection of the material. Some embodiments would not require such a hatch 110.

Figure 3:
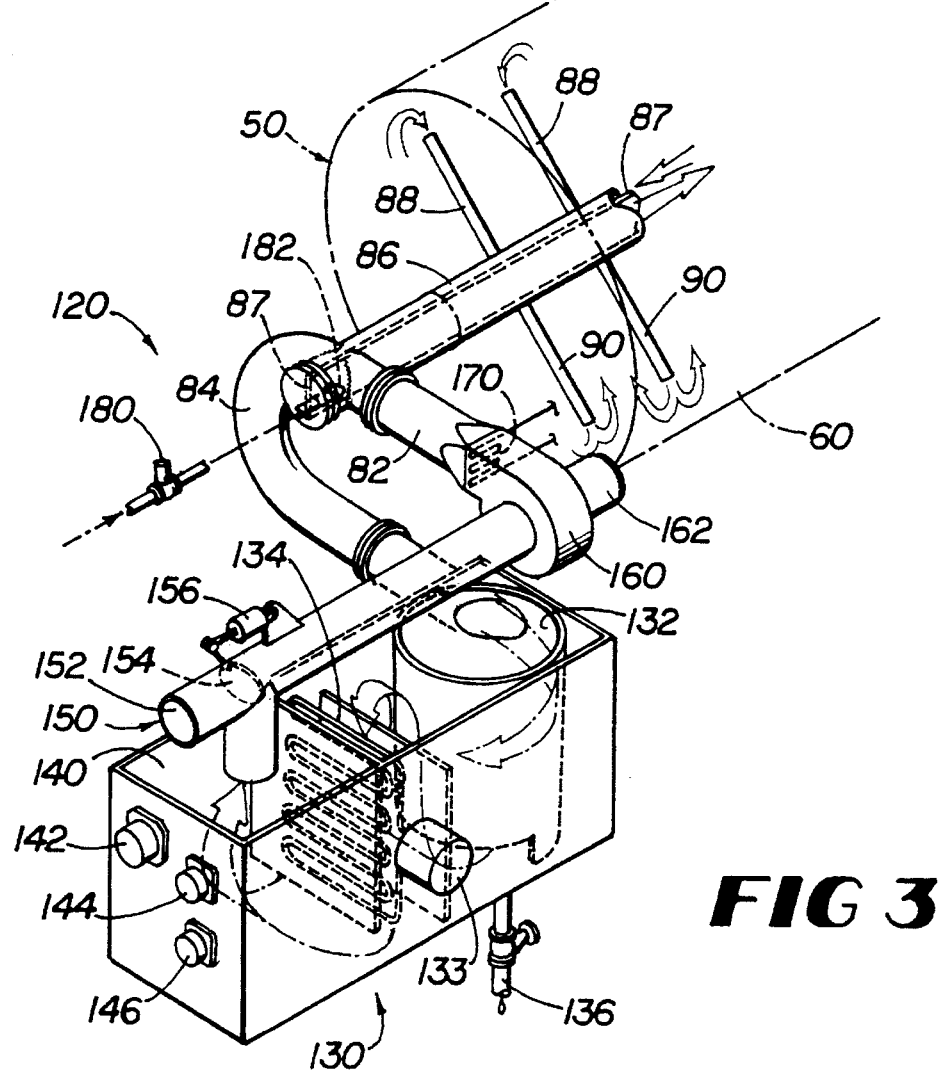
FIG. 3 is a perspective view of one end of the reaction vessel, showing the air flow mechanism and the environmental control means.

Referring to FIG. 3, air exiting the enclosure 31 through the air return flange 84 passes into the air treatment and monitoring plenum 130. In the treatment and monitoring plenum 130, the air first passes through a cyclonic separator drum 132, where any large particles or water droplets are removed from the air as it circulates around the drum 132. The air then passes through a heat exchanger/dehumidifier unit 134, which is capable of both removing heat and condensing water vapor from the air as it cools down. A drain 136 allows condensed water to be removed from the system.

The air then passes through an air sensing chamber 140 where it comes in contact with an $O_2$ sensor 142, a $CO_2$ sensor 144, and a humidity sensor 146. These sensors could comprise remote sensors which generate electronic signals representative of the corresponding sensed values or the they could comprise nonelectronic sensors used in local operation. After passing through the air sensing chamber 140, the air flows into a blower 160 which blows it back into the enclosure 31 through the air introduction flange 82 and the manifold 86.

Figure 4:
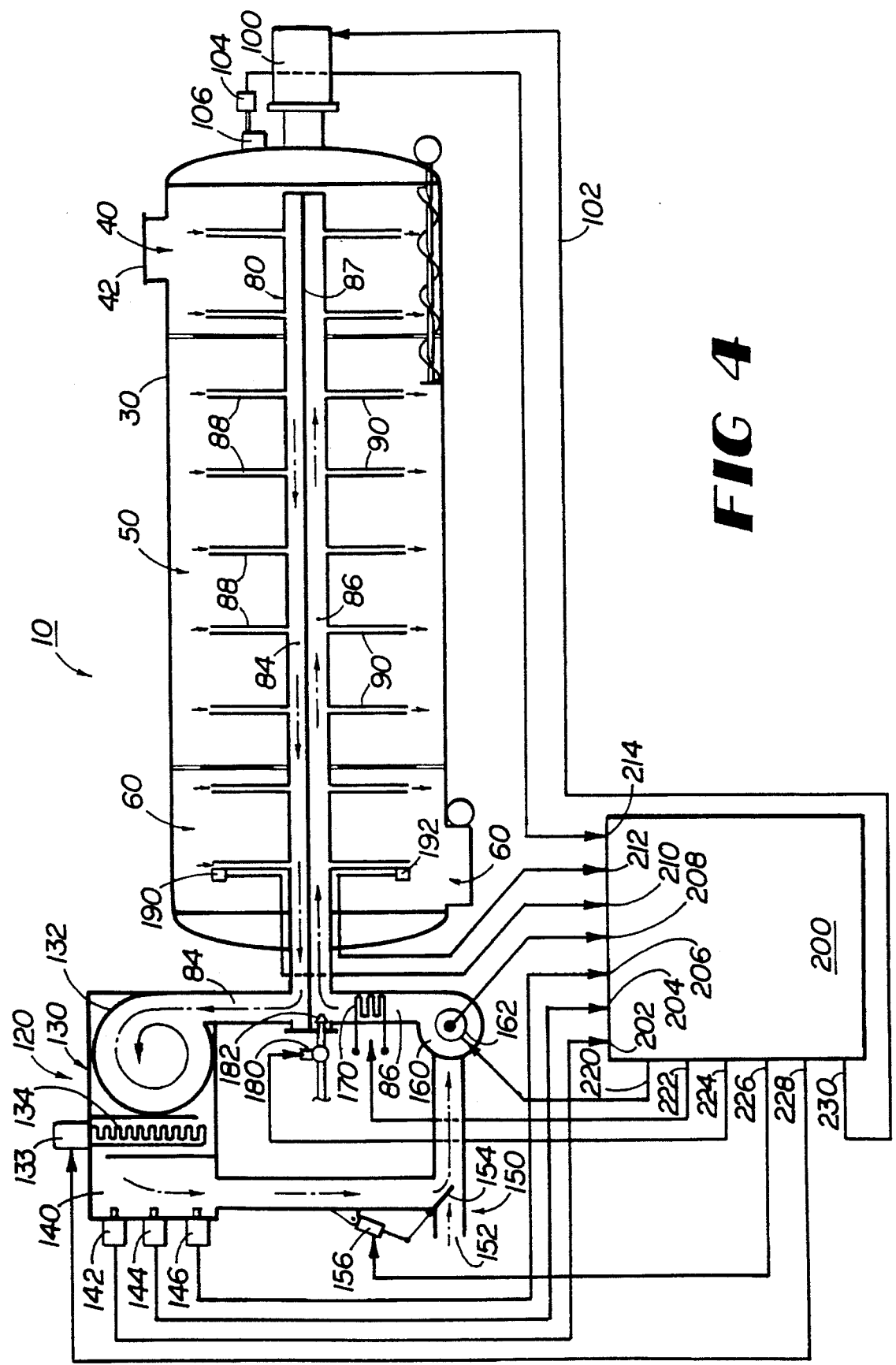
FIG. 4 is a schematic representation of a control system in conjunction with the reactor enclosure in accordance with the present invention.

FIG. 4 is a schematic diagram showing one preferred embodiment of the environmental control system 120 in accordance with the present invention. Generally, a computer 200 controls the environmental parameters within the enclosure 31. Any general purpose digital computer would work if fitted with suitable interface electronics (such as an IBM-compatible PC fitted with an IEEE-488 bus). An embedded microprocessor could be used, as well as a dedicated industrial process control computer. Manual control could also be employed in some embodiments.

Rotation of the housing 30 is caused by the motor 100. The computer 200 has a motor speed control output 230 which sends an activation signal via a speed control line 102 to the motor 100. A limit switch 104 is disposed in fixed relation to the rotating housing 30 and engages a detent 106 affixed to the housing each time the detent 106 passes by the switch 104 causing it to generate pulses to a position signal input 214 to the computer 200 that can be used by the computer both to determine the rotational speed of the housing 30 and to determine position of the receiving hatch 42.

The computer 200 also generates a dehumidifier activation control output 228 which activates the compressor of the heat exchanger/dehumidifier 134. Control of the heat exchanger/dehumidifier 134 is based on three sensor inputs to the computer: an air temperature input 210 which receives a signal from an air temperature transducer 190 disposed in the enclosure 31; a pile temperature input 212 which receives a signal from a pile temperature transducer 192 disposed in the enclosure 31; and the humidity input 206 which receives a signal from the humidity sensor 146 in the air sensing chamber 140. When the computer 200 determines that humidity needs to be removed from the air, or that the air is too hot, it activates the heat exchanger/dehumidifier compressor 133 via a dehumidifier control output 228. Similarly, if the temperature is too low, the computer generates a heater control output 222 that activates a series of heating coils 170 placed in front of the blower 160.

Information from the humidity 146 sensor is used to control the addition of water as well. When water is to be added to the system, the computer 200 generates a water spray control output 224 that opens a solenoid-controlled water valve 180 which allows water to pass through a spray nozzle 182 into the air manifold 86.

The $O_2$ sensor 142 generates an $O_2$ sensor input 202 and the $CO_2$ sensor 144 generates a $CO_2$ sensor input 204 to the computer, which generates an $O_2$-add control signal 226 when the oxygen level falls below, or the carbon dioxide level falls above, the value necessary for decomposition of the particular type of material being composted. In one embodiment, oxygen is added when the $O_2$-add control signal 226 activates a new air assembly 150, which comprises a solenoid 156 which opens a valve 154 at an air intake 152, allowing fresh air to pass into the blower 160. In alternative embodiments, a compressed air or oxygen system could be employed in the new air assembly 150. Similarly, $CO_2$ can be removed from the system by opening a vent. This could be done using the new air assembly 150 as a discharge vent, rather than as an intake.

The air flow rate through the system is controlled by the computer 200 generating a blower speed control output signal 220 that activates the blower 160. The blower 160 may have a revolution encoder 164 which generates a blower speed feedback input 208 to the computer 200.

If desired, the computer 200 could also display sensory and process control information. This information could be displayed with analog means if computer control is not used in the particular embodiment being employed.

Although environmental control of the above embodiment is performed by a digital computer, it should be appreciated that some, or all, of the above-mentioned parameters could be controlled either manually or by analog electrical means. The decision as to which method of control to be employed for any parameter depends on the particular application involved. It should also be appreciated that, depending on the application, it may not be necessary to control all of the above parameters. It should also be appreciated that additional parameters might need to be controlled in certain applications. It should also be appreciated that the selection of the parameters to be controlled would be obvious to one skilled in the art.

In operating the present invention, certain additional reactants may have to be added to the material in order to achieve the desired result. Also, it may be necessary to add solidifiers (e.g. sawdust) to certain materials (e.g. municipal waste) to maintain the material at the proper consistency for decomposition.

Although the above embodiment of the present invention is designed especially to compost municipal waste, it should be appreciated that the present invention could be easily configured to decompose other types of material, such as agricultural waste, silage, timber waste and the like. The present invention could also be employed to reclaim polluted soil and other polluted materials.

The above embodiments are given as illustrative examples and are not intended to impose any limitations on the invention. It will be readily appreciated that many deviations may be made from the specific embodiments disclosed in this specification without departing from the invention. Accordingly it is intended to cover all such modifications as within the scope of this invention.

What is claimed is:

1. A reaction vessel for biologically decomposing a material, comprising:

a. a frame;

b. an airtight housing, having a longitudinal axis, rotatably mounted on the frame, defining an enclosure therein, the enclosure having an upper portion and an opposite lower portion, the housing defining a first aperture for receiving the material into the enclosure and a second aperture for discharging the material from the enclosure;

c. means for controlling environmental conditions within the enclosure so that biological decomposition of the material can occur at a controlled rate;

d. means for rotating the housing about the longitudinal axis;

e. an elongated manifold, disposed coaxially with the longitudinal axis, having an air supply side and an opposite air return side, the air supply side and the air return side separated by a wall disposed therebetween, the manifold defining a first plurality of spaced apart openings diposed so that the lower portion of the enclosure is in fluid communication with the air supply side, the manifold also defining a second plurality of spaced apart openings disposed so the upper portion of the enclosure is in fluid communication with the air return side; and f. means for circulating air into the enclosure through the air supply side, through the material and out of the enclosure through the air return side.

2. The vessel of claim 1 further comprising means for agitating the material in the enclosure.

3. The vessel of claim 2 wherein the means for agitating comprises means for rotating the housing.

4. The vessel of claim 3 further comprising means to control the rotational speed of the housing.

5. The vessel of claim 4 wherein the means for rotating the housing comprises a motor coupled to the housing so that the motor causes the housing to rotate at a rate determined by a current input to the motor, and wherein the means to control the rotational speed of the housing comprises:

a. a computer that generates a speed control signal; and b. a relay, responsive to the speed control signal that generates a current representative of the speed control signal.

6. The vessel of claim 1 wherein the means for controlling the environmental conditions comprises:

a. means for circulating air through the enclosure in a closed loop so that air leaving the enclosure will be recirculated back into the enclosure; and b. means to control the air recirculation rate within the enclosure.

7. The vessel of claim 6 wherein the air recirculation rate control means comprises:

a. a computer which generates a blower speed control signal representative of a predetermined blower speed; and b. a blower, in fluid communication with the air circulating means, responsive to the blower speed control signal, that causes air to flow through the air circulating means at a rate corresponding to the blower speed control signal.

8. The vessel of claim 6 wherein the means for controlling the environmental conditions further comprises means, operatively coupled to the circulating means, for controlling the oxygen level of the air inside the enclosure.

9. The vessel of claim 8 wherein the oxygen level control means comprises:

a. an oxygen sensor that generates a signal representative of the oxygen level inside the enclosure;

b. means for adding oxygen to the air recirculating in the enclosure; and c. a computer, responsive to the signal from the oxygen sensor, which compares the received signal from the oxygen sensor to a preselected value of oxygen level and then generates an oxygen activation signal that activates the oxygen adding means when the oxygen level falls below the preselected value of oxygen level.

10. The vessel of claim 9 wherein the oxygen adding means comprises:

a. an oxygen supply; and b. an electrically activated valve responsive to the oxygen activation signal, in fluid communication with the oxygen supply and the enclosure, that allows oxygen from the oxygen supply to pass into the enclosure upon receiving the oxygen activation signal.

11. The vessel of claim 6 wherein the means for controlling the environmental conditions further comprises means, operatively coupled to the circulating means, for controlling the humidity of the air inside the enclosure.

12. The vessel of claim 11 wherein the humidity control means comprises:

a. a humidity sensor that generates a signal representative of the humidity of the air inside the enclosure;

b. means for adding water to the air in the enclosure;

c. means for removing humidity from the air in the enclosure; and d. a computer, responsive to the signal from the humidity sensor, which compares the received signal from the humidity sensor to a preselected value of humidity and then generates:

i. a humidity addition activation signal that activates the water adding means when the humidity falls below the fist preselected value of humidity level; and ii. a humidity removal activation signal that activates the means for removing humidity when the humidity rises above a second preselected humidity level.

13. The vessel of claim 12 wherein the water adding means comprises:

a. a water supply;

b. a water spray nozzle in fluid communication with the enclosure; and b. an electrically activated valve responsive to the water spray activation signal, in fluid communication with the water supply and the water spray nozzle, that allows water from the water supply to pass through the water spray nozzle into the enclosure upon receiving the water spray activation signal.

14. The vessel of claim 12 wherein the humidity removing means comprises a dehumidifier through which the air recirculating in the enclosure passes.

15. The vessel of claim 6 wherein the means for controlling the environmental conditions further comprises means, operatively coupled to the circulating means, for controlling the temperature of the air inside the enclosure.

16. The vessel of claim 15 wherein the temperature control means comprises:

a. a temperature sensor that generates a signal representative of the temperature of the air inside the enclosure;

b. means for adding heat to the air in the enclosure;

c. means for removing heat from the air in the enclosure; and d. a computer, responsive to the signal from the temperature sensor, which compares the received signal from the temperature sensor to a first preselected value of temperature and a second preselected value of temperature, and then generates:

i. a heat addition activation signal that activates the heat adding means when the temperature falls below the first preselected value of temperature; and ii. a heat removal activation signal that activates the means for removing heat when the temperature rises above the second preselected value of temperature.

17. The vessel of claim 16 wherein the heat adding means comprises a heater in thermal communication with the enclosure and responsive to the heat addition activation signal, which adds heat to the enclosure upon receiving the heat addition activation signal.

18. The vessel of claim 16 wherein the heat removing means comprises a heat exchanger in thermal communication with the enclosure and responsive to the heat removing activation signal, which removes heat from the enclosure upon receiving the heat removing activation signal.

19. The vessel of claim 6 wherein the means for controlling the environmental conditions further comprises means, operatively coupled to the circulating means, for controlling the carbon dioxide level of the air inside the enclosure.

20. The vessel of claim 19 wherein the carbon dioxide level control means comprises:

a. a carbon dioxide level sensor that generates a signal representative of the carbon dioxide level of the air inside the enclosure;

b. means for removing carbon dioxide from the air in the enclosure; and c. a computer, responsive to the signal from the carbon dioxide level sensor, which compares the received signal from the carbon dioxide level sensor to a preselected value of carbon dioxide level and then generates a carbon dioxide removal activation signal that activates the carbon dioxide removal means when the carbon dioxide level rises above the preselected value of carbon dioxide level.

21. The vessel of claim 20 wherein the means for removing carbon dioxide comprises:

a. a vent in fluid communication with the enclosure; and b. a valve in fluid communication with the vent and responsive to the carbon dioxide removal activation signal that allows air from inside the enclosure to exit the enclosure when the carbon dioxide level of the air in the enclosure rises above the preselected value of carbon dioxide level.

22. The vessel of claim 1 wherein the axis of rotation of the housing is disposed at an incline relative to the frame so that the material introduced into the enclosure proximal to the higher portion of the housing tends to flow toward the lower portion of the housing.

23. The vessel of claim 22 further comprising means to adjust the amount of inclination of the housing.

24. The vessel of claim 23 wherein the means to adjust the amount of inclination comprises a hydraulic jack.

25. The vessel of claim 1 further comprising:

a. a separating wall disposed within the enclosure generally perpendicular to the axis of rotation, forming therein a first chamber and a second chamber, the first chamber and the second chamber capable of containing the material; and b. means for moving the material from the first chamber to the second chamber, secured to the housing so that as the material is moved from the first chamber to the second chamber the housing remains airtight.

26. The vessel of claim 25 wherein the means for moving the material comprises a screw-type conveyor disposed within the enclosure.

27. The vessel of claim 1 wherein the housing has an inside surface and further comprising a protuberance disposed on the inside surface to break up clumps of the material.

* * * * *